United States Patent
Weiner et al.

(10) Patent No.: US 9,719,505 B2
(45) Date of Patent: Aug. 1, 2017

(54) MEDICATION PUMP TEST DEVICE AND METHOD OF USE

(71) Applicant: Medtronic MiniMed, Inc., Northridge, CA (US)

(72) Inventors: Matthew A. Weiner, Sherman Oaks, CA (US); David L. Canfield, Lake Hughes, CA (US); Carl A. Link, Los Angeles, CA (US); Edward C. Morrow, Porter Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 15/182,301

(22) Filed: Jun. 14, 2016

(65) Prior Publication Data

US 2016/0290333 A1    Oct. 6, 2016

Related U.S. Application Data

(63) Continuation of application No. 14/223,725, filed on Mar. 24, 2014, now Pat. No. 9,388,805.

(51) Int. Cl.
| | |
|---|---|
| *F04B 51/00* | (2006.01) |
| *G01B 13/14* | (2006.01) |
| *A61M 5/142* | (2006.01) |

(52) U.S. Cl.
CPC ............ *F04B 51/00* (2013.01); *A61M 5/142* (2013.01); *G01B 13/14* (2013.01); *A61M 2209/02* (2013.01)

(58) Field of Classification Search
CPC ................. G01B 13/14; F04B 51/00
USPC ............................................ 73/168
See application file for complete search history.

(56) References Cited

U.S. PATENT DOCUMENTS

| | | | | |
|---|---|---|---|---|
| 4,216,585 A | * | 8/1980 | Hatter | G01B 5/18 33/836 |
| 4,505,278 A | * | 3/1985 | Alban | A61B 5/0053 600/398 |
| 4,755,173 A | | 7/1988 | Konopka et al. | |
| 4,760,847 A | * | 8/1988 | Vaillancourt | A61M 39/0208 128/907 |
| 5,292,309 A | * | 3/1994 | Van Tassel | A61M 25/06 604/116 |
| 5,391,250 A | | 2/1995 | Cheney, II et al. | |
| 5,485,408 A | | 1/1996 | Blomquist | |
| 5,522,803 A | | 6/1996 | Teissen-Simony | |

(Continued)

*Primary Examiner* — Lisa Caputo
*Assistant Examiner* — Jamel Williams
(74) *Attorney, Agent, or Firm* — Medtronic Minimed, Inc.

(57) ABSTRACT

A medication pump test device and method of use including a test device for use with a medication pump and a depth indicator, the test device including: an external body portion defining a depth indicator recess operable to receive the fixed portion of the depth indicator; an internal body portion attached to the external body portion, the internal body portion defining a slide spindle passage operable to allow free axial movement of the slide spindle of the depth indicator. The test device maintains the fixed portion of the depth indicator at a fixed axial position along the central axis relative to the medication pump when the fixed portion of the depth indicator is seated in the depth indicator recess, the external contact portion contacts the medication pump, and the internal body portion is seated in the open end of the reservoir compartment.

20 Claims, 10 Drawing Sheets

(56) References Cited

U.S. PATENT DOCUMENTS

| | | |
|---|---|---|
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,200,274 B1* | 3/2001 | McNeirney ............ A61B 90/06 128/897 |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2* | 1/2012 | Moberg ............ A61M 5/14244 604/131 |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0027429 A1* | 2/2007 | Kuracina ............... A61M 5/158 604/116 |
| 2007/0100288 A1* | 5/2007 | Bozeman ................ A61M 5/20 604/181 |
| 2007/0123819 A1 | 5/2007 | Mernoe et al. |
| 2010/0160861 A1* | 6/2010 | Causey, III ......... A61M 5/1456 604/131 |

\* cited by examiner

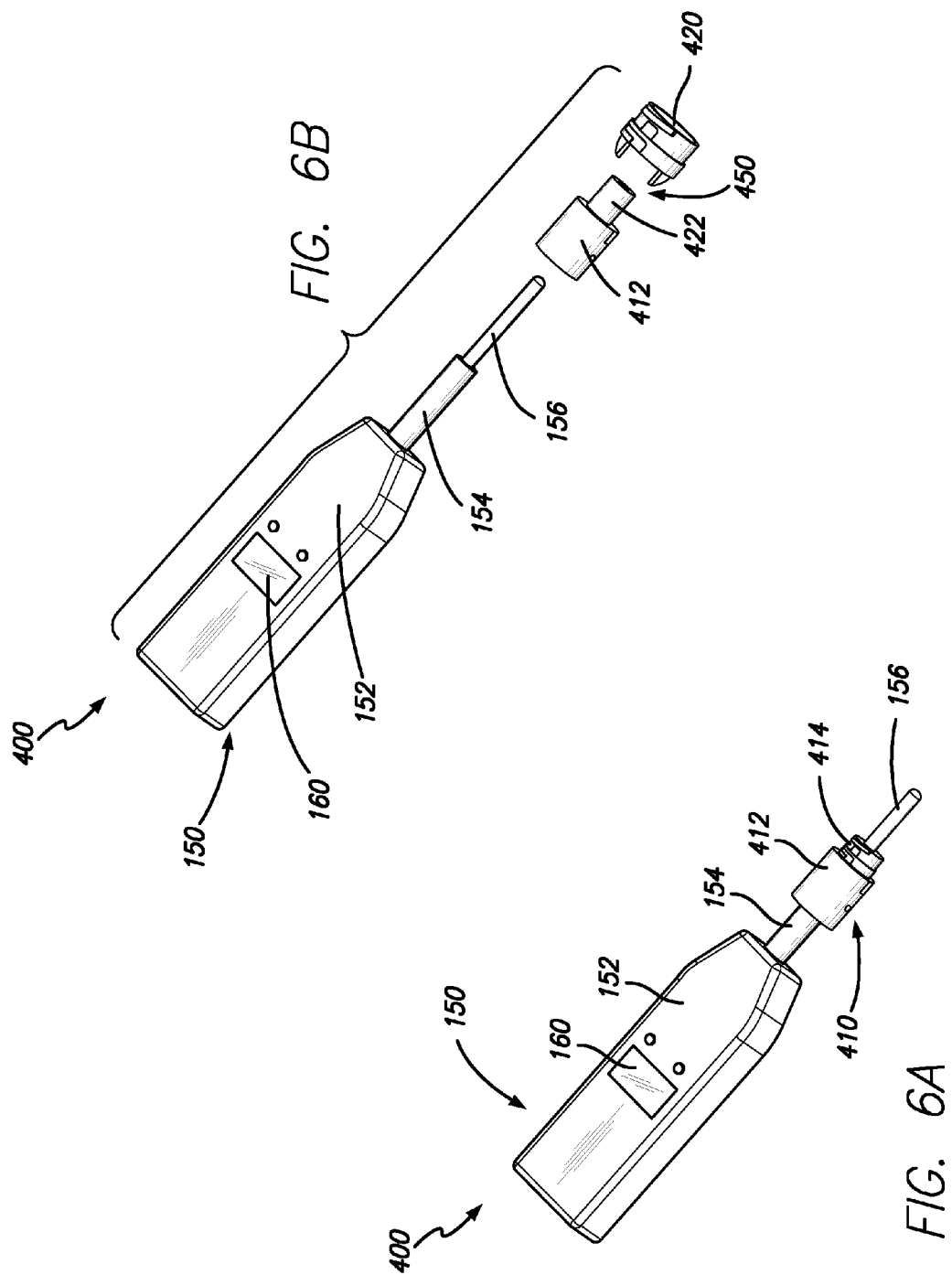

MEDICATION PUMP TEST DEVICE AND METHOD OF USE

RELATED APPLICATION

The present disclosure is a Continuation of U.S. patent application Ser. No. 14/223,725, filed on Mar. 24, 2014, the contents of which are incorporated herein by reference in their entirety.

TECHNICAL FIELD

The technical field of this disclosure is testing devices and methods, particularly, medication pump test devices and methods of use.

BACKGROUND OF THE INVENTION

Accuracy and repeatability are required for any reliable test method. This is particularly important for testing of medical devices in which an error in testing can result in failing to administer the desired dosage of a therapeutic agent. One such device is a wearable medication pump.

A wearable medication pump, such as an insulin pump, is a small device about the size of a small cell phone that is worn externally. The wearable medication pump delivers precise doses of a therapeutic agent to a patient by injection, and can be adjusted manually and/or through feedback sensors to closely match the patient's needs. The therapeutic agent is typically held within a reservoir installed in a reservoir compartment in the wearable medication pump. A pump motor slide advances a piston in the reservoir to deliver the therapeutic agent to the patient.

Because the dose of therapeutic agent delivered is a function of pump motor slide position, testing of the wearable medication pump must assure that the pump motor slide does not move unnecessarily and only moves the distance requested to deliver the desired dose. One method of measuring pump motor slide position is to insert a ruler into the reservoir compartment until the ruler contacts the pump motor slide, then note the distance from a point on the wearable medication pump casing to the point where the ruler contacts the pump motor slide. Another method of measuring pump motor slide position is to position a caliper against the pump casing, advance the caliper depth probe into the reservoir compartment until the depth probe contacts the pump motor slide, then read the distance on the caliper.

Unfortunately, such distance measurement methods are neither accurate nor repeatable. The person performing the test can place the ruler or caliper depth probe into the reservoir compartment at different angles. When reading the distance on the ruler, the person performing the tests can use different landmarks points on the wearable medication pump casing. The test results can vary in a single test and can vary even more over a number of tests when different persons are likely to be performing the test. This, in turn, prevents achievement of highest product quality, product reliability, and patient safety.

It would be desirable to have a medication pump test devices and methods of use that would overcome the above disadvantages.

SUMMARY OF THE INVENTION

One aspect of the invention provides a test device for use with a medication pump and a depth indicator, the medication pump defining a reservoir compartment having an open end with an open end diameter, the depth indicator having a fixed portion and a slide spindle slideably connected to the fixed portion, the test device including: an external body portion having an external diameter greater than the open end diameter, the external body portion defining a depth indicator recess operable to receive the fixed portion of the depth indicator; an internal body portion attached to the external body portion, the internal body portion having an external diameter less than the open end diameter and defining a slide spindle passage operable to allow free axial movement of the slide spindle of the depth indicator, a junction of the internal body portion and the external body portion defining an external contact portion. The depth indicator recess and the slide spindle passage are in communication along a central axis of the test device, and the test device maintains the fixed portion of the depth indicator at a fixed axial position along the central axis relative to the medication pump when the fixed portion of the depth indicator is seated in the depth indicator recess, the external contact portion contacts the medication pump, and the internal body portion is seated in the open end of the reservoir compartment.

Another aspect of the invention provides a test system for use with a medication pump, the medication pump defining a reservoir compartment having an open end with an open end diameter, the test system including: a depth indicator having a fixed portion and a slide spindle slideably connected to the fixed portion; and a test device affixed to the depth indicator. The test device includes: an external body portion having an external diameter greater than the open end diameter, the external body portion defining a depth indicator recess operable to receive the fixed portion of the depth indicator; an internal body portion attached to the external body portion, the internal body portion having an external diameter less than the open end diameter and defining a slide spindle passage operable to allow free axial movement of the slide spindle of the depth indicator, a junction of the internal body portion and the external body portion defining an external contact portion. The depth indicator recess and the slide spindle passage are in communication along a central axis of the test device, and the test device maintains the fixed portion of the depth indicator at a fixed axial position along the central axis relative to the medication pump when the fixed portion of the depth indicator is seated in the depth indicator recess, the external contact portion contacts the medication pump, and the internal body portion is seated in the open end of the reservoir compartment.

Another aspect of the invention provides a method of testing a medication pump, the medication pump defining a reservoir compartment having an open end and including a pump motor slide disposed in the reservoir compartment, the method including: providing a medication pump test system including a depth indicator and a test device affixed to the depth indicator, the depth indicator having a fixed portion and a slide spindle slideably connected to the fixed portion, the depth indicator providing a depth measurement in response to position of the slide spindle, the test device having an external body portion and an internal body portion attached to the external body portion, a junction of the internal body portion and the external body portion defining an external contact portion, the external body portion being attached to the fixed portion of the depth indicator and the internal body portion defining a slide spindle passage operable to allow free axial movement of the slide spindle of the depth indicator; seating the internal body portion of the test device in the open end of the reservoir compartment with the external contact portion of the test device in contact with the medication pump; contacting a face of the pump motor slide with a tip of the slide spindle; recording a first depth measurement from the depth indicator; and subjecting the medication pump to test conditions.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 6A-6C are an assembled view, exploded view, and a detail exploded view, respectively, of a medication pump test device made in accordance with the invention and a depth indicator.

DETAILED DESCRIPTION

Figure 1:
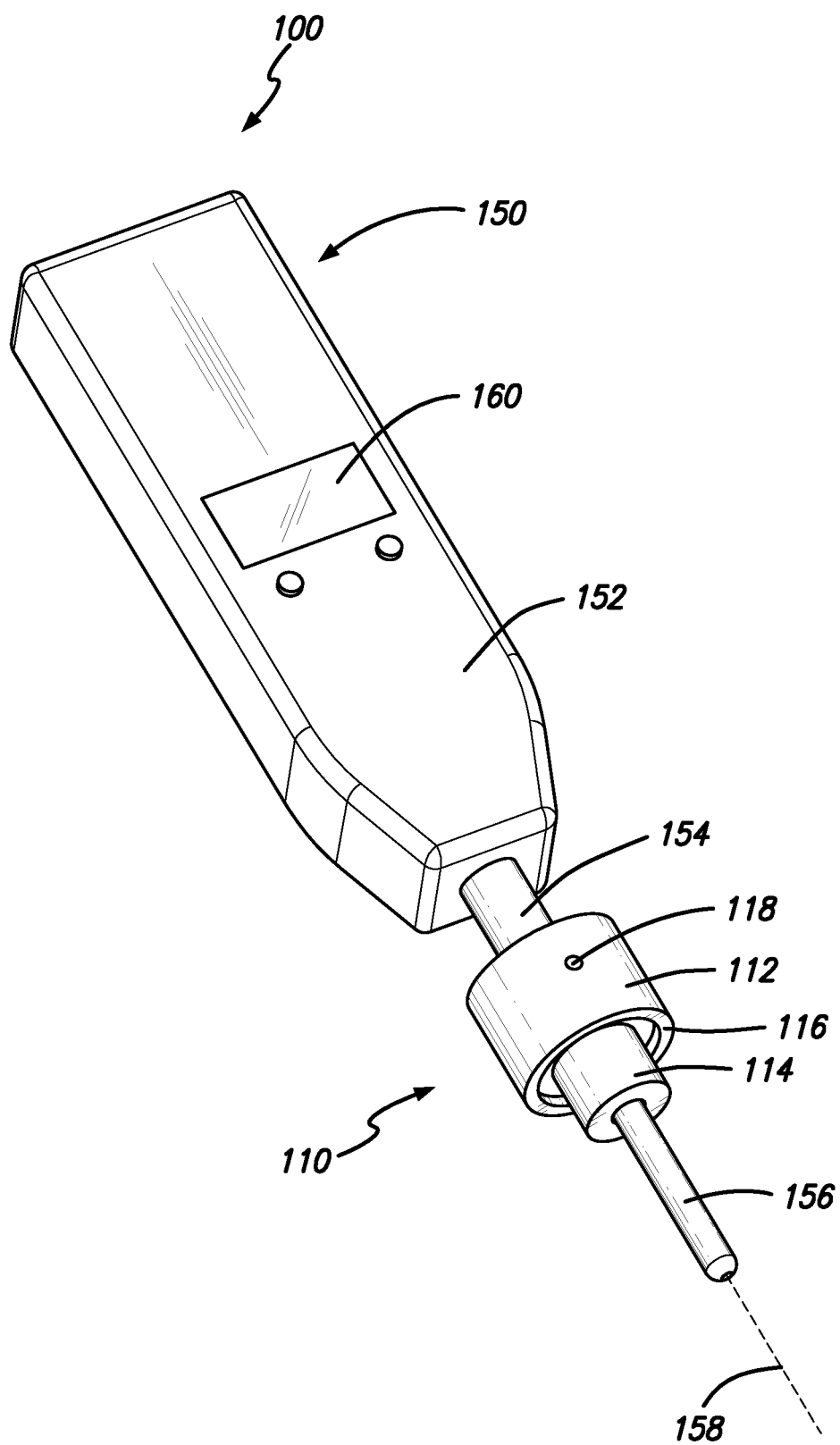
FIG. 1 is a perspective view of a medication pump test system made in accordance with the invention.

FIG. 1 is a perspective view of a medication pump test system made in accordance with the invention. The medication pump test system 100 includes a test device 110 installed on a depth indicator 150. The test device 110 fixes the position of the depth indicator 150 relative to a medication pump under test to make the measurements of pump motor slide position accurate and repeatable.

The depth indicator 150 includes an indicator body 152 and a fixed stem 154, which form a portion of the depth indicator 150, and a slide spindle 156, which is slideably disposed in the fixed stem 154 to allow the slide spindle 156 to move axially along the slide spindle centerline 158. The depth indicator 150 can also include a depth display 160. In operation, the depth display 160 indicates the change in axial position of the slide spindle 156 relative to the fixed stem 154. In this example, the depth indicator 150 is an electronic depth indicator, such as the Mitutoyo 575-123 Digimatic Indicator, or the Mitutoyo 543-472B Digimatic Indicator, available from the Mitutoyo America Corporation of Aurora, Ill. Those skilled in the art will appreciate that the depth indicator 150 need not be electronic and that a mechanical depth indicator can be used for particular applications as desired.

The test device 110 includes an external body portion 112, and internal body portion 114 attached to the external body portion 112, and an external contact portion 116 defined by the junction of the internal body portion 114 and the external body portion 112. The internal body portion 114 has an external diameter sized to fit within the reservoir compartment of a medication pump. The external body portion 112 has an external diameter greater than an open end diameter of the reservoir compartment of the medication pump, so that the external body portion 112 remains outside of the reservoir compartment during measurement. The external contact portion 116 contacts the medication pump so that the fixed portion of the depth indicator 150 is held at a fixed axial position relative to the medication pump during measurement. In one embodiment, the external diameter of the internal body portion 114 is selected to be slightly smaller than the open end diameter of the reservoir compartment, so that a friction fit holds the test device 110 in the reservoir compartment during measurement. In this example, the test device 110 also includes a set screw 118 to secure the test device 110 to the fixed stem 154 of the depth indicator 150.

Figure 2:
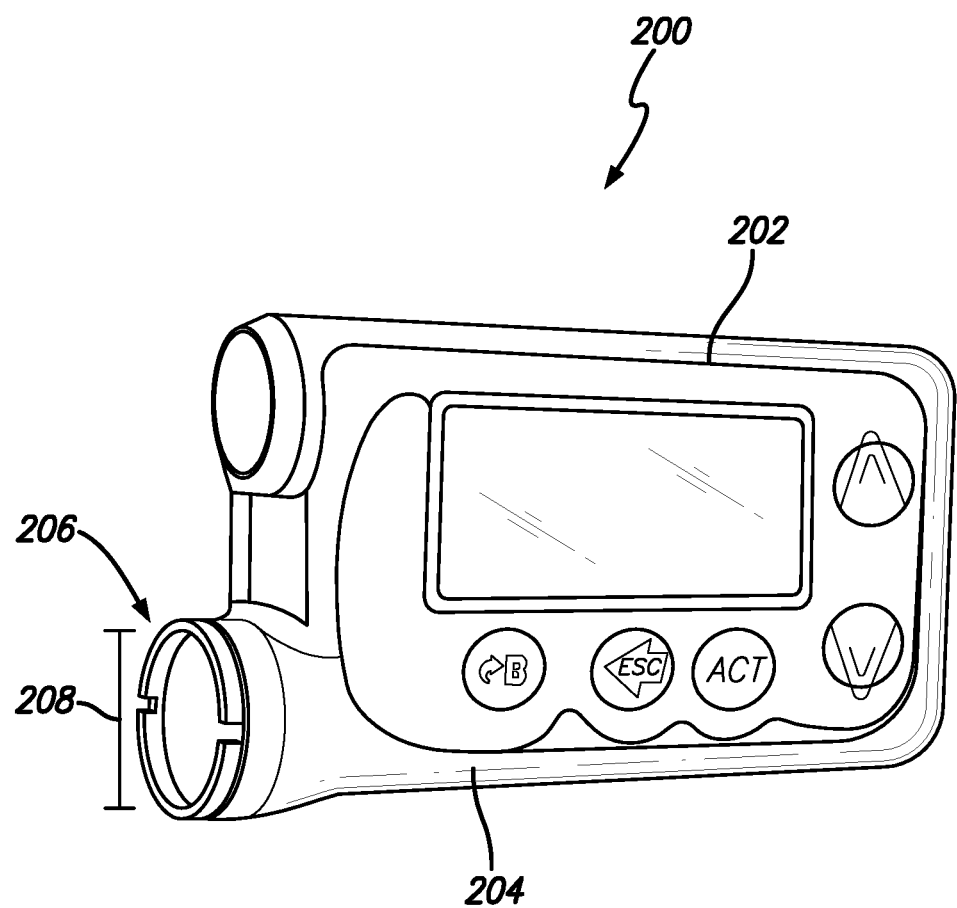
FIG. 2 is a photograph of a medication pump for use with a medication pump device made in accordance with the invention.

FIG. 2 is a photograph of a medication pump for use with a medication pump device made in accordance with the invention. The medication pump 200 has a medication pump body 202 and defines a reservoir compartment 204 operable to receive a reservoir containing a therapeutic agent. The reservoir compartment 204 has an open end 206 with an open end diameter 208. During measurement, the internal body portion of the test device is seated in the open end 206 of the reservoir compartment 204 and the external contact portion of the test device is in contact with the medication pump 200, such as being in contact with the medication pump body 202 at the open end 206.

Figure 3:
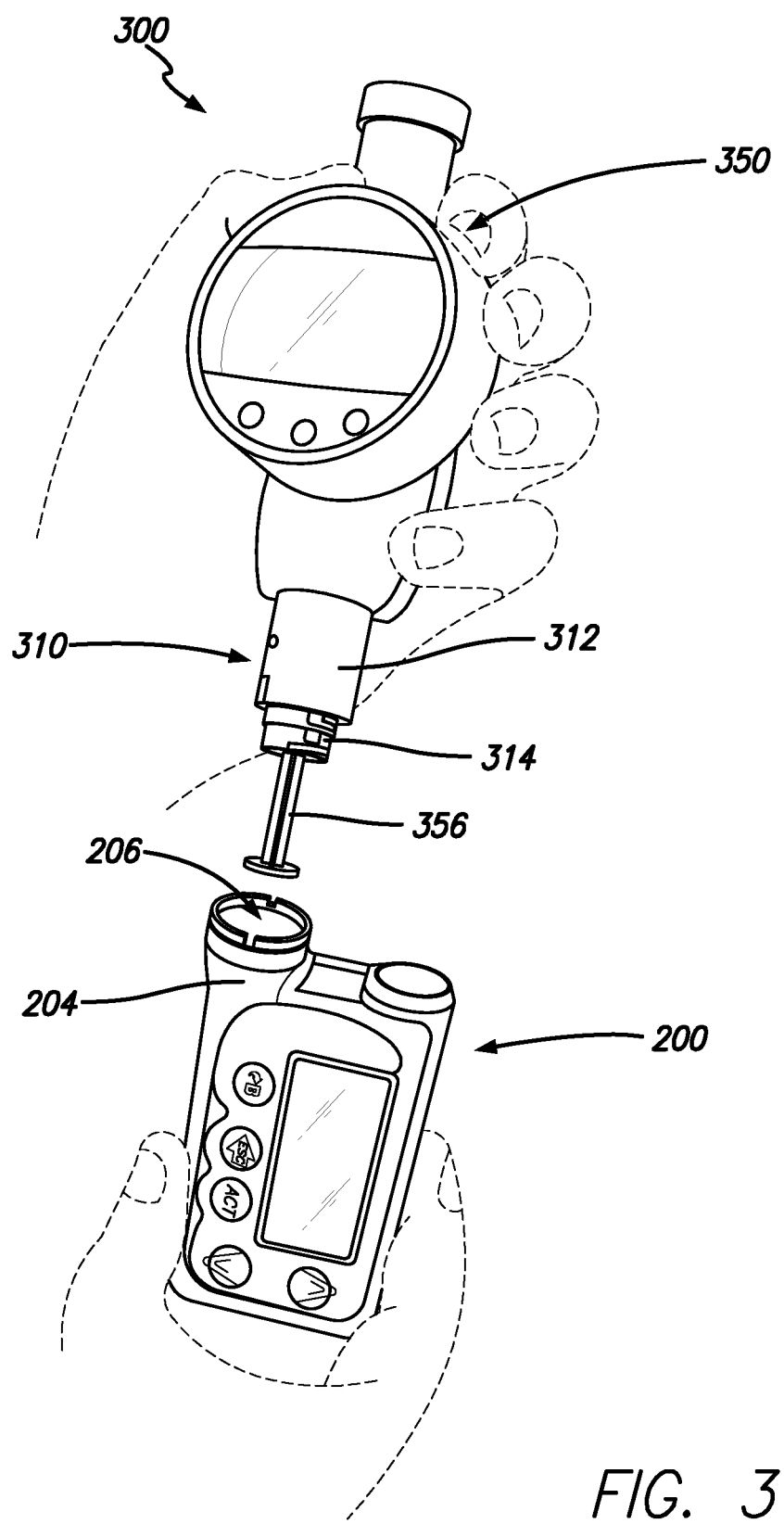
FIG. 3 is a photograph of a medication pump test device made in accordance with the invention, a depth indicator, and a medication pump.

FIG. 3, in which like elements share like reference numbers with FIG. 2, is a photograph of a medication pump test device made in accordance with the invention, a depth indicator, and a medication pump. In FIG. 3, the medication pump test system 300 has the internal body portion 314 of the test device 310 and the slide spindle 156 of the depth indicator 350 aligned for positioning within the reservoir compartment 204 of the medication pump 200. The external body portion 312 remains outside the reservoir compartment 204 during measurement.

Figure 4C:
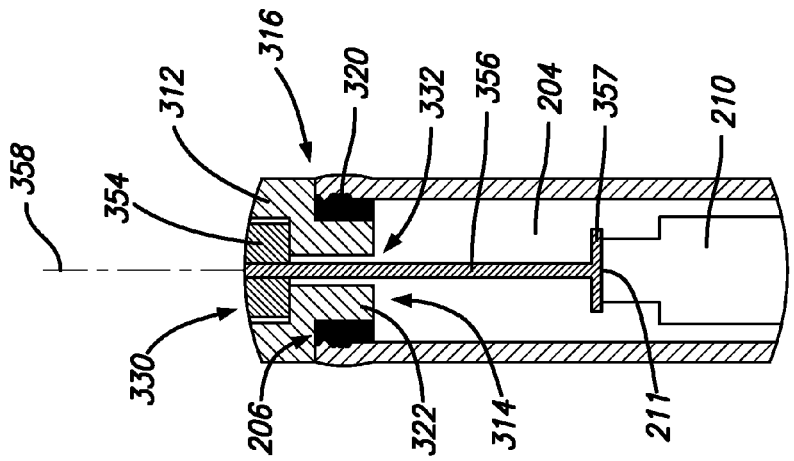
FIGS. 4A-4C are a pre-inserted view, inserted view, and a detail cross section view, respectively, of a medication pump test device made in accordance with the invention, a depth indicator, and a medication pump.
Figure 4B:
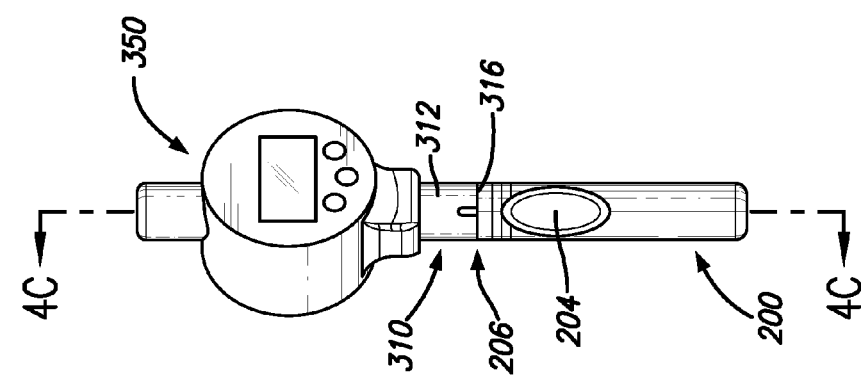
Figure 4A:
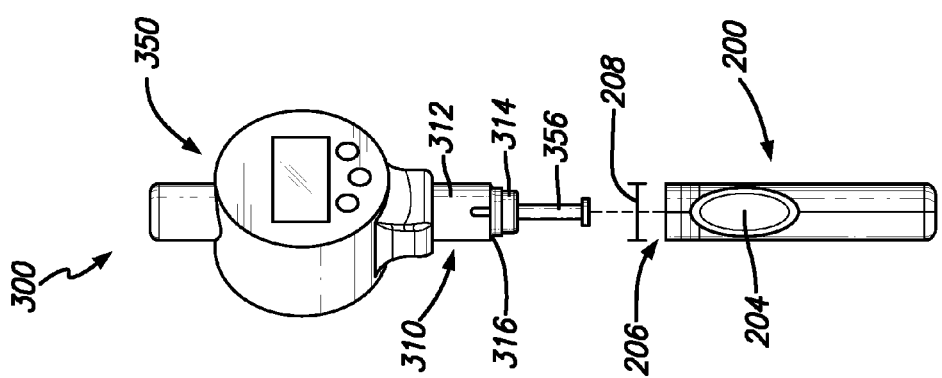

FIGS. 4A-4C, in which like elements share like reference numbers with FIGS. 2&3, are a pre-inserted view, inserted view, and a detail cross section view, respectively, of a medication pump test device made in accordance with the invention, a depth indicator, and a medication pump.

Referring to FIG. 4A, the internal body portion 314 of the test device 310 and the slide spindle 156 of the depth indicator 350 are aligned for positioning within the reservoir compartment 204 of the medication pump 200. The external body portion 312 of the test device 310 has an external diameter greater than the open end diameter 208 of the open end 206 of the reservoir compartment 204, so that the external body portion 312 remains outside the reservoir compartment 204 during measurement. The internal body portion 314 is attached to the external body portion 312, and has an external diameter less than the open end diameter 208 so that the internal body portion 314 can be seated within the open end 206 of the reservoir compartment 204. In one embodiment, the external diameter of the internal body portion 314 is selected to be slightly smaller than the open end diameter 208 of the reservoir compartment, so that a friction fit holds the test device 310 in the reservoir compartment 204 during measurement. The junction of the internal body portion 314 and the external body portion 312 define an external contact portion 316, which contacts the medication pump 200 during measurement.

Referring to FIG. 4B, the internal body portion of the test device 310 has been positioned within the reservoir compartment 204 of the medication pump 200 and the external body portion 312 of the medication pump 200 remains outside the reservoir compartment 204. The external contact portion 316 is in contact with the medication pump 200.

FIG. 4C is a detail cross section of the depth indicator 350, medication pump 200, and test device 310 assembled as an FIG. 4B axially along the slide spindle centerline 358 of the slide spindle 356 of the depth indicator 350. Referring to FIG. 4C, the internal body portion 314 of the test device 310 in this example includes two parts: a test device adapter 322 and a medication pump connector 320 disposed around the test device adapter 322. Also in this example, the medication pump connector 320 and the open end 206 of the reservoir compartment 204 have complementary threads so that the test device 310 is held in the reservoir compartment 204 during measurement.

The external body portion 312 defines a depth indicator recess 330 operable to receive the fixed portion of the depth indicator 350, which in this example is the fixed stem 354 of the depth indicator 350 which is seated in the depth indicator recess 330. The internal body portion 314 defines a slide spindle passage 332 operable to allow free axial movement of the slide spindle 356 of the depth indicator 350. The depth indicator recess 330 and the slide spindle passage 332 are in communication along a central axis of the test device 310 which is: your with the slide spindle centerline 358. The test device 310 maintains the fixed stem 354 (fixed portion) of the depth indicator 350 at a fixed axial position along the slide spindle centerline 358 (central axis) relative to the medication pump 200 when the fixed stem 354 (fixed portion) of the depth indicator 350 is seated in the depth indicator recess 330, the external contact portion 316 contacts the medication pump 200, and the internal body portion 314 is seated in the open end 206 of the reservoir compartment 204.

During measurement, the slide spindle 356 is free to move axially relative to the fixed stem 354 of the depth indicator 350. The tip 357 of the slide spindle 356 can contact the face 211 of the pump motor slide 210 to measure the distance between the fixed stem 354 and the face 211 of the pump motor slide 210. The depth indicator 350 is a fixed position relative to the medication pump 200, so that accurate and repeatable measurement of the position of the pump motor slide 210 are possible.

Figure 5A:
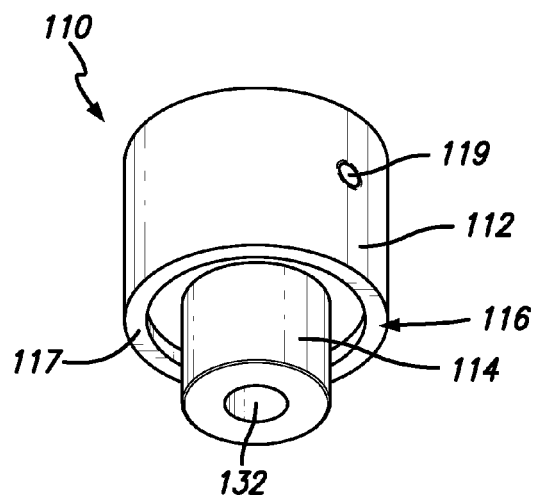
FIGS. 5A-5C are a perspective view, side view, and a cross section view, respectively, of a medication pump test device made in accordance with the invention.
Figure 5B:
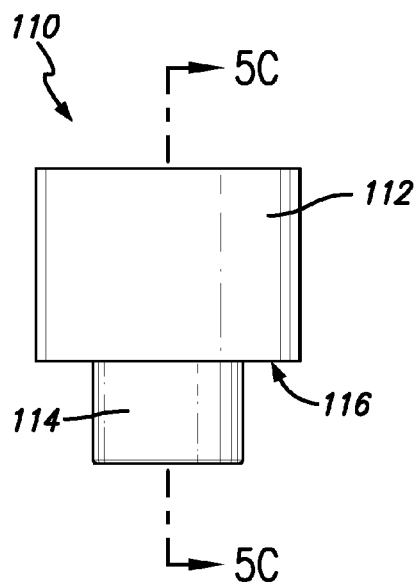
Figure 5C:
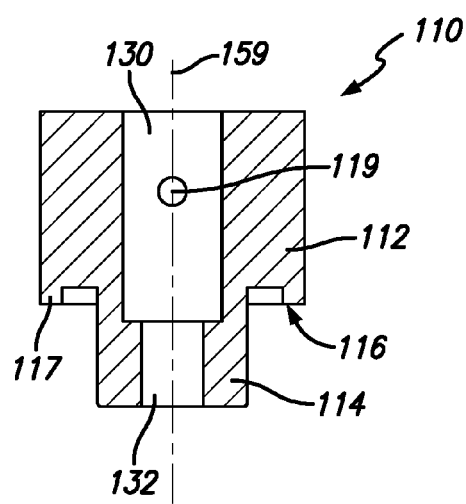

FIGS. 5A-5C, in which like elements share like reference numbers within these figures and with FIG. 1, are a perspective view, side view, and a cross section view, respectively, of a medication pump test device made in accordance with the invention. The test device 110 includes an external body portion 112 and an internal body portion 114 attached to the external body portion 112. The junction of the internal body portion 114 and the external body portion 112 define an external contact portion 116, which in this example includes a ring projection 117 to assure positive contact with the medication pump. The test device 110 can be made of any material, such as plastic, metal, or the like, as desired for a particular application. In one example, the test device 110 can be made of a polycarbonate plastic.

The external body portion 112 has an external diameter greater than the open end diameter of the reservoir compartment. The external body portion 112 defines a depth indicator recess 130 operable to receive the fixed portion of the depth indicator. Those skilled in the art will appreciate that the depth indicator recess 130 can be sized and shaped to receive the fixed portion of any depth indicator desired for a particular application. In one example, the fixed portion is a fixed stem of the depth indicator. In another example, the fixed portion is a portion of the indicator body of the depth indicator. The fixed portion as defined herein can be any portion of the depth indicator which is fixed relative to the slide spindle.

The internal body portion 114 has an external diameter less than the open end diameter of the reservoir compartment. The internal body portion 114 defines a slide spindle passage 132 operable to allow free axial movement of the slide spindle of the depth indicator. In one embodiment, the external diameter of the internal body portion 114 is selected to be slightly smaller than the open end diameter of the reservoir compartment, so that a friction fit holds the test device 110 in the reservoir compartment during measurement. In this example, the test device 110 also includes a threaded opening 119 to secure the test device 110 to the fixed stem 154 of the depth indicator 150 with a set screw. In another example, the test device 110 can be secured to the fixed stem 154 by a friction fit. In yet another example, the test device 110 can be secured to the fixed stem 154 with an adhesive, such as an ultraviolet cured adhesive or the like. The depth indicator recess 130 and the slide spindle passage 132 are in communication along a central axis 159 of the test device 110.

Figure 6C:
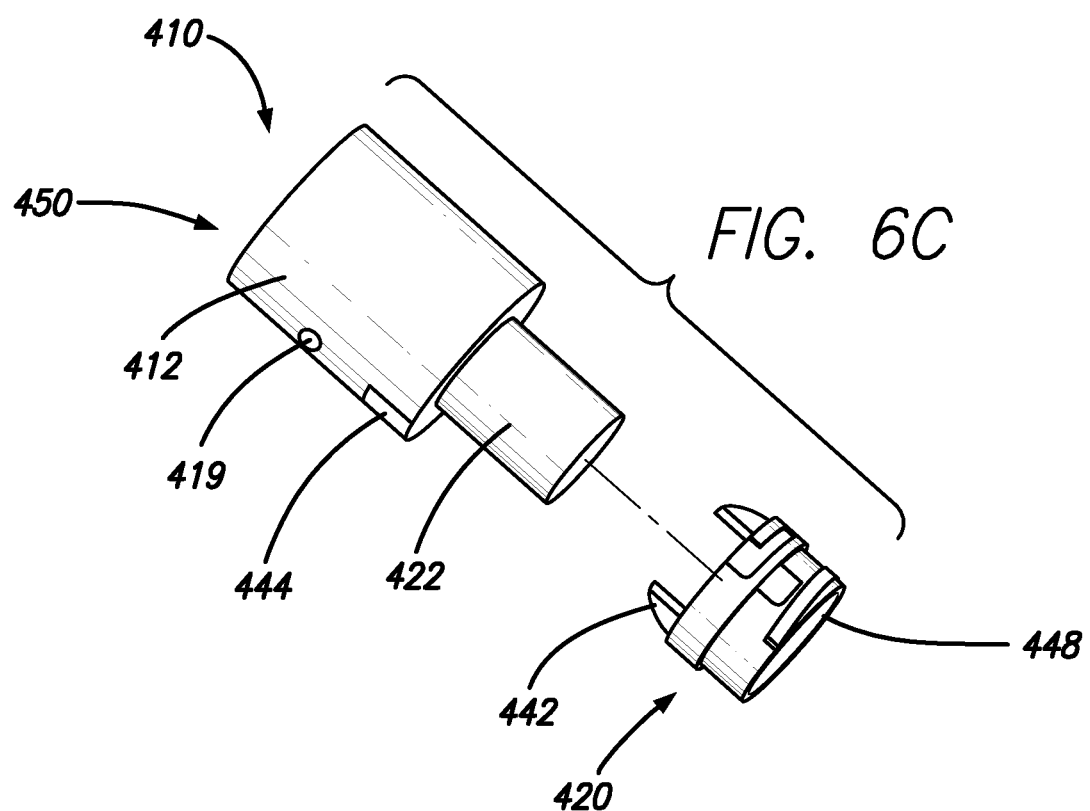

FIGS. 6A-6C, in which like elements share like reference numbers within these figures and with FIG. 1, are an assembled view, exploded view, and a detail exploded view, respectively, of a medication pump test device made in accordance with the invention and a depth indicator. Referring to FIGS. 6A-6C, the internal body portion 414 of the test device 410 in this example includes two parts: a test device adapter 422 and a medication pump connector 420 disposed around the test device adapter 422. In one embodiment, the medication pump connector 420 is a connector normally used by the patient to secure a therapeutic agent reservoir within the reservoir compartment of the medication pump, with an adapter opening formed in the standard connector to receive the test device adapter 422. In one embodiment, the medication pump connector 420 and the open end of the reservoir compartment have complementary threads so that the test device 410 is held in the reservoir compartment during measurement.

The medication pump test system 400 includes a test device 410 installed on a depth indicator 150, which is described in detail in the description of FIG. 1. The test device 410 is affixed to the depth indicator 150 at the fixed stem 154 with the slide spindle 156 extending from the internal body portion 414 of the test device 410.

Referring to FIG. 6B, the medication pump test system 400 is illustrated with the test device 410, which includes the test device adapter 422 and the medication pump connector 420, removed from the depth indicator 150 and the medication pump connector 420 removed from the test device adapter 422.

Referring to FIG. 6C, the test device 410 is illustrated with the medication pump connector 420 removed from the test device adapter 422 of the test device component 450. In one example, the medication pump connector 420 can be secured to the test device adapter 422 by a friction fit. In another example, the medication pump connector 420 can be secured to the test device adapter 422 with an adhesive, such as an ultraviolet cured adhesive or the like.

The test device component 450 includes an external body portion 412 and a test device adapter 422 attached to the external body portion 412. The junction of the test device adapter 422 with the medication pump connector installed and the external body portion 412 define an external contact portion 416. In this example, the test device component 450 includes a threaded opening 419 to secure the test device 110 to the fixed stem of the depth indicator with a set screw. In another example, the test device component 450 can be secured to the fixed stem by a friction fit. In yet another example, the test device component 450 can be secured to the fixed stem with an adhesive, such as an ultraviolet cured adhesive or the like.

In this embodiment, the medication pump connector 420 is a connector normally used by the patient to secure a therapeutic agent reservoir within the reservoir compartment of the medication pump, with an adapter opening 440 formed in the standard connector to receive the test device adapter 422. In this embodiment, the medication pump connector 420 includes threads 448 complementary to threads in the open end of the reservoir compartment to hold the test device in the reservoir compartment during measurement. In this embodiment, the medication pump connector 420 includes optional wings 442 complementary to the slots 444 in the external body portion 412 to maintain radial alignment between the test device adapter 422 and the medication pump connector 420.

Figure 7:
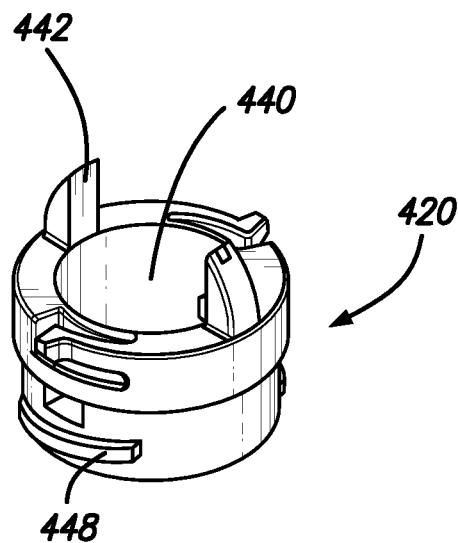
FIG. 7 is a perspective view of a medication pump connector for use in a medication pump test device made in accordance with the invention.

FIG. 7, in which like elements share like reference numbers with FIGS. 6A-6C, is a perspective view of a medication pump connector for use in a medication pump test device made in accordance with the invention. In this embodiment, the medication pump connector 420 is a connector normally used by the patient to secure a therapeutic agent reservoir within the reservoir compartment of the medication pump, with an adapter opening 440 formed in the standard connector to receive the test device adapter 422. In this embodiment, the medication pump connector 420 includes threads 448 complementary to threads in the open end of the reservoir compartment to hold the test device in the reservoir compartment during measurement. In this embodiment, the medication pump connector 420 includes optional wings 442 complementary to the slots 444 in the external body portion 412 to maintain radial alignment between the test device adapter 422 and the medication pump connector 420.

The external diameter of the medication pump connector 420 is the external diameter of the internal body portion 414 of the test device 410. The internal body portion 414 has an external diameter less than the open end diameter of the reservoir compartment. In another embodiment, the threads 448 can be omitted and the external diameter of the internal body portion 414 is selected to be slightly smaller than the open end diameter of the reservoir compartment, so that a friction fit holds the test device 410 in the reservoir compartment during measurement. The medication pump connector 420 can be made of any material, such as plastic, metal, or the like, as desired for a particular application. In one example, the medication pump connector 420 can be made of polycarbonate plastic.

Figure 8A:
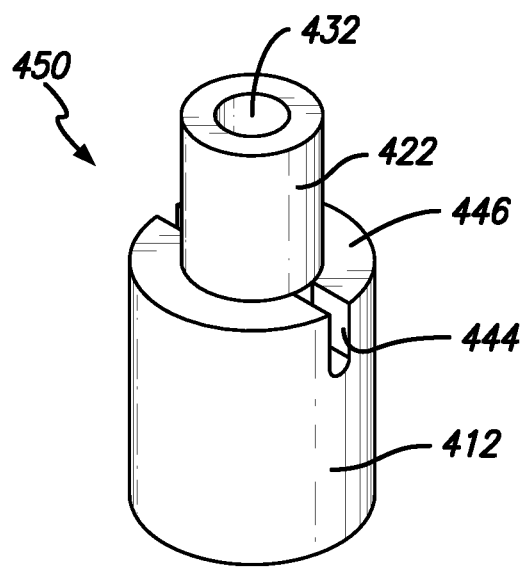
FIGS. 8A-8C are a perspective view, side view, and a cross section view, respectively, of a test device component for use in a medication pump test device made in accordance with the invention.
Figure 8B:
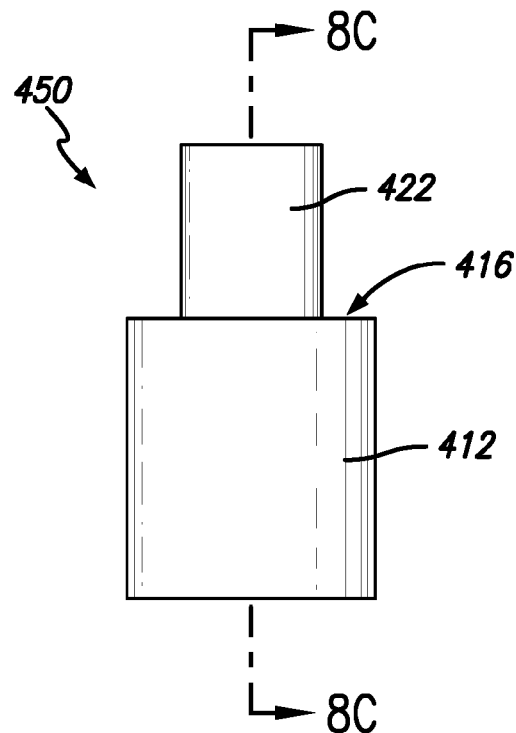
Figure 8C:
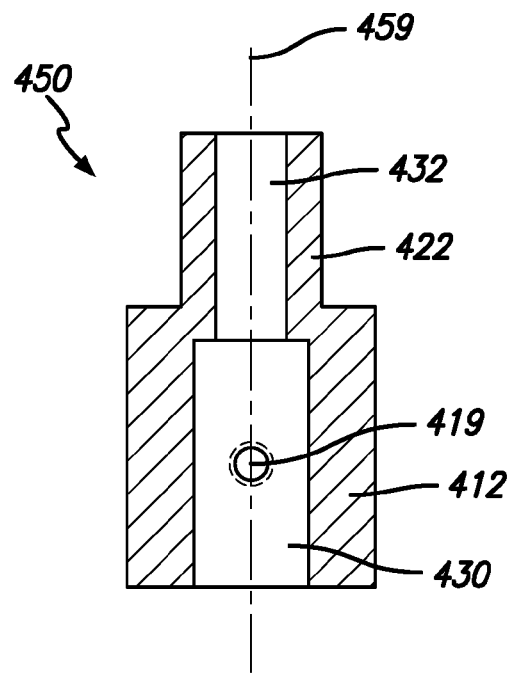

FIGS. 8A-8C, in which like elements share like reference numbers within the figures and with FIGS. 6A-6C, are a perspective view, side view, and a cross section view, respectively, of a test device component for use in a medication pump test device made in accordance with the invention.

The test device component 450 includes an external body portion 412 and a test device adapter 422 attached to the external body portion 412. The junction of the test device adapter 422 with the medication pump connector installed and the external body portion 412 define an external contact portion 416. The test device component 450 can be made of any material, such as plastic, metal, or the like, as desired for a particular application. In one example, the test device component 450 can be made of a polycarbonate plastic.

The external body portion 412 has an external diameter greater than the open end diameter of the reservoir compartment. The external body portion 412 defines a depth indicator recess 430 operable to receive the fixed portion of the depth indicator. Those skilled in the art will appreciate that the depth indicator recess 430 can be sized and shaped to receive the fixed portion of any depth indicator desired for a particular application. In one example, the fixed portion is a fixed stem of the depth indicator. In another example, the fixed portion is a portion of the indicator body of the depth indicator. The fixed portion as defined herein can be any portion of the depth indicator which is fixed relative to the slide spindle.

In this example, the test device component 450 includes a threaded opening 419 to secure the test device 110 to the fixed stem of the depth indicator with a set screw. In another example, the test device component 450 can be secured to the fixed stem by a friction fit. In yet another example, the test device component 450 can be secured to the fixed stem with an adhesive, such as an ultraviolet cured adhesive or the like.

The test device adapter 422 has an external diameter sized to fit the adapter opening of the medication pump connector. In one embodiment, the external diameter of the test device adapter 422 is selected to be slightly smaller than the adapter opening, so that a friction fit holds the medication pump connector on the test device component 450. In another embodiment, the medication pump connector is held on the test device component 450 with an adhesive, such as an ultraviolet cured adhesive or the like. The test device adapter 422 defines a slide spindle passage 432 operable to allow free axial movement of the slide spindle of the depth indicator. The depth indicator recess 430 and the slide spindle passage 432 are in communication along a central axis 459 of the test device 410.

Figure 9:
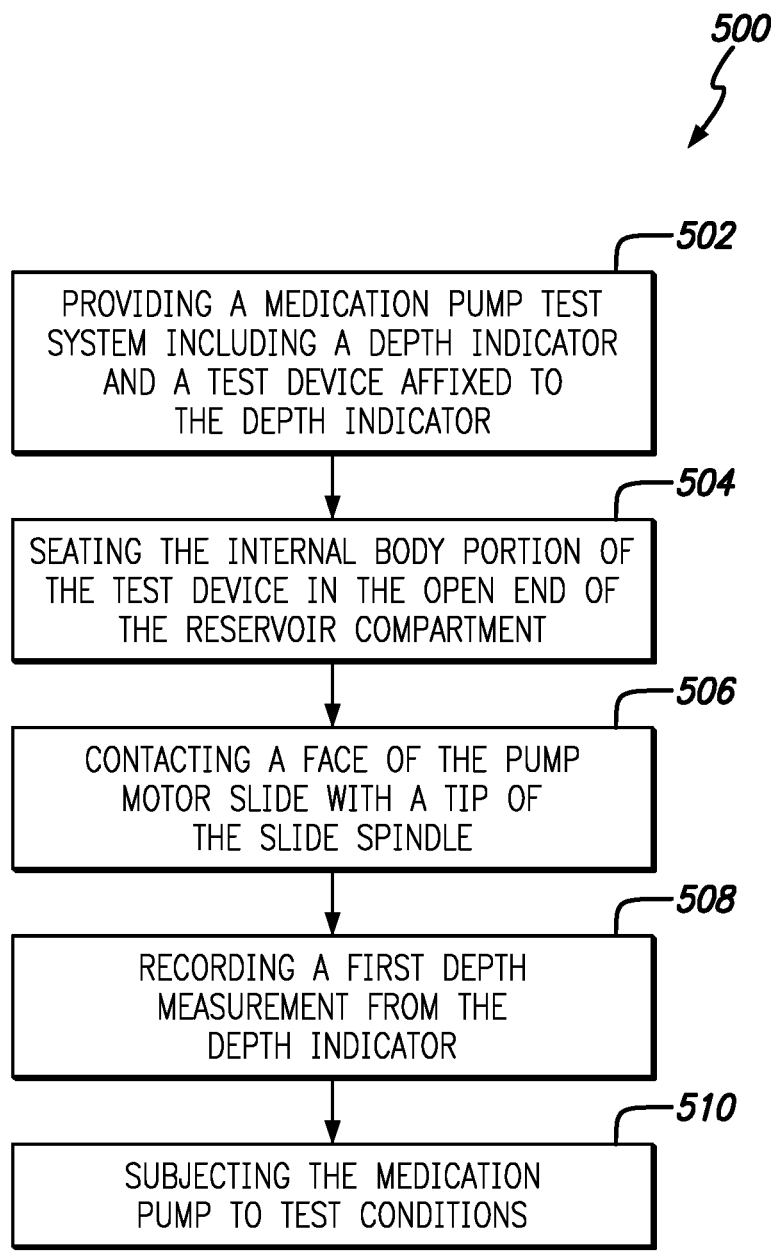
FIG. 9 is a flow chart of a method of use for a medication pump test device in accordance with the invention.

FIG. 9 is a flow chart of a method of use for a medication pump test device in accordance with the invention. The test method 500 for testing a medication pump, the medication pump defining a reservoir compartment having an open end and including a pump motor slide disposed in the reservoir compartment, includes: providing a medication pump test system including a depth indicator and a test device affixed to the depth indicator 502, the depth indicator having a fixed portion and a slide spindle slideably connected to the fixed portion, the depth indicator providing a depth measurement in response to position of the slide spindle, the test device having an external body portion and an internal body portion attached to the external body portion, a junction of the internal body portion and the external body portion defining an external contact portion, the external body portion being attached to the fixed portion of the depth indicator and the internal body portion defining a slide spindle passage operable to allow free axial movement of the slide spindle of the depth indicator; seating the internal body portion of the test device in the open end of the reservoir compartment 504 with the external contact portion of the test device in contact with the medication pump; contacting a face of the pump motor slide with a tip of the slide spindle 506; recording a first depth measurement from the depth indicator 508; and subjecting the medication pump to test conditions 510.

The subjecting the medication pump to test conditions 510 can include subjecting the medication pump to any test conditions desired for a particular application. Exemplary test conditions include vibration, temperature levels, temperature cycling, humidity levels, humidity cycling, pump motor slide cycling, electromagnetic field exposure, electrostatic discharge exposure, drops from height, impact, water submersion, and the like.

The test method 500 can be used to determine whether the pump motor slide position changes after the medication pump has been subjected to test conditions. The test method 500 can further include recording a second depth measurement from the depth indicator after the subjecting; and calculating change in position of the pump motor slide from a difference between the first depth measurement and the second depth measurement.

The test method 500 can include removing the test system from the medication pump before the medication pump is subjected to test conditions. The test method 500 can further include removing the internal body portion of the test device from the open end of the reservoir compartment after the recording and before the subjecting; seating the internal body portion of the test device in the open end of the reservoir compartment with the external contact portion of the test device in contact with the medication pump after the subjecting; contacting the face of the pump motor slide with the tip of the slide spindle; recording a second depth measurement from the depth indicator; and calculating change in position of the pump motor slide from a difference between the first depth measurement and the second depth measurement.

The test method 500 can be used to determine that the pump motor slide moves the desired distance to deliver the desired amount of therapeutic agent. The medication pump has a pump motor operable to move the pump motor slide, and the subjecting the medication pump to test conditions includes: energizing the pump motor to move the pump motor slide from a first axial position where the first depth measurement was recorded to a second axial position; contacting the face of the pump motor slide with the tip of the slide spindle at the second axial position; recording a second depth measurement from the depth indicator; and calculating change in position of the pump motor slide from a difference between the first depth measurement and the second depth measurement. In one embodiment, the slide spindle is biased (e.g., with a spring) to maintain the tip of the slide spindle in contact with the face of the pump motor slide when the pump motor moves the pump motor slide from the first axial position to the second axial position, so that the tip of the slide spindle remains in contact the face of the pump motor as the pump motor slide moves between the two axial positions.

It is important to note that FIGS. 1-9 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A test system comprising:
    a depth indicator comprising a fixed portion; and
    a test device installed on the depth indicator, the test device comprising:
        an internal body portion; and
        an external body portion that defines a depth indicator recess that receives the fixed portion of the depth indicator, wherein a junction of the internal body portion and the external body portion define an external contact portion that contacts a medication pump,
    wherein the test device maintains the fixed portion of the depth indicator at a fixed axial position along a central axis relative to the medication pump when the fixed portion of the depth indicator is seated in the depth indicator recess, the external contact portion contacts the medication pump, and the internal body portion is seated in an open end of a reservoir compartment of the medication pump.

2. The test system of claim 1, wherein the fixed portion of the depth indicator further comprises a fixed stem, and the test device is installed on the depth indicator at the fixed stem.

3. The test system of claim 1, wherein the test device comprises a material including at least one of a plastic or a metal.

4. The test system of claim 1, wherein the depth indicator further comprises a slide spindle and the internal body portion defines a slide spindle passage that allows free axial movement of the slide spindle of the depth indicator.

5. The test system of claim 1, wherein the central axis comprises a slide spindle centerline relative to the medication pump.

6. The test system of claim 1, wherein the medication pump further comprises a pump motor slide disposed in the reservoir compartment.

7. The test system of claim 6, wherein the depth indicator further comprises a slide spindle that includes a tip that contacts a face of the pump motor slide to measure a distance between the fixed portion and the face of the pump motor slide.

8. The test system of claim 1, wherein the depth indicator further comprises a display.

9. The test system of claim 1, wherein the internal body portion has an external diameter sized to fit within the reservoir compartment of the medication pump.

10. The test system of claim 1, wherein the external body portion has an external diameter greater than the open end of the reservoir compartment of the medication pump.

11. A method comprising:
    seating a fixed portion of a depth indicator in a depth indicator recess defined by an external body portion of a test device;
    contacting, at an external contact portion defined by a junction of an internal body portion of the test device and the external body portion of the test device, a medication pump under test; and
    maintaining, by the test device, the fixed portion of the depth indicator at a fixed position relative to the medication pump when the fixed portion of the depth indicator is seated in the depth indicator recess, the external contact portion contacts the medication pump, and the internal body portion is seated in an open end of a reservoir compartment of the medication pump.

12. The method of claim 11, wherein the medication pump further comprises a pump motor slide disposed in the reservoir compartment, and the depth indicator further comprises a slide spindle that includes a tip that contacts a face of the pump motor slide, the method further comprising measuring a distance between the fixed portion and the face of the pump motor slide.

13. The method of claim 12, further comprising repeating the measuring to determine a position of the pump motor slide.

14. The method of claim 11, wherein the depth indicator further comprises a slide spindle slideably connected to the fixed portion, the method further comprising providing a depth measurement in response to a position of the slide spindle.

15. A test system comprising:
a depth indicator comprising a fixed portion fixed relative to a slide spindle; and
a test device installed on the depth indicator at the fixed portion, wherein the test device fixes a position of the depth indicator relative to a medication pump under test, wherein the medication pump comprises a reservoir compartment having an open end, the test device comprising:
an internal body portion that defines a slide spindle passage that allows free axial movement of the slide spindle of the depth indicator; and
an external body portion attached to the internal body, wherein a junction of the internal body portion and the external body portion define an external contact portion that contacts the medication pump, and the external body defines a depth indicator recess that receives the fixed portion of the depth indicator,
wherein the test device maintains the fixed portion of the depth indicator at a fixed axial position along a central axis relative to the medication pump when the fixed portion of the depth indicator is seated in the depth indicator recess, the external contact portion contacts the medication pump, and the internal body portion is seated in the open end of the reservoir compartment of the medication pump.

16. The medication pump test system of claim 15, wherein the fixed portion of the depth indicator further comprises a fixed stem.

17. The medication pump test system of claim 15, wherein the fixed portion of the depth indicator further comprises a portion of an indicator body of the depth indicator.

18. The medication pump test system of claim 15, wherein the internal body portion of the test device further comprises a test device adapter and a medication pump connector disposed around the test device adapter.

19. The medication pump test system of claim 15, wherein the central axis comprises a slide spindle centerline relative to the medication pump.

20. The medication pump test system of claim 15, wherein the medication pump further comprises a pump motor slide disposed in the reservoir compartment, wherein the slide spindle further comprises a tip that contacts a face of the pump motor slide to measure a distance between the fixed portion and the face of the pump motor slide.

\* \* \* \* \*